US006250757B1

(12) United States Patent
Roffman et al.

(10) Patent No.: US 6,250,757 B1
(45) Date of Patent: Jun. 26, 2001

(54) HYBRID REFRACTIVE BIREFRINGENT MULTIFOCAL OPHTHALMIC LENSES

(75) Inventors: Jeffrey H. Roffman; Khalid Chehab, both of Jacksonville, FL (US)

(73) Assignee: Johnson & Johnson Vision Products, Inc., Jacksonville, FL (US)

( * ) Notice: Subject to any disclaimer, the term of this patent is extended or adjusted under 35 U.S.C. 154(b) by 0 days.

(21) Appl. No.: 09/466,301

(22) Filed: Dec. 15, 1999

(51) Int. Cl.$^7$ ............................................. G02C 7/04
(52) U.S. Cl. ............................................. 351/161
(58) Field of Search .................... 351/161, 164, 351/168, 159, 160 R, 160 H; 623/6.24, 6.27, 6.28, 6.3; 359/494

(56) References Cited

U.S. PATENT DOCUMENTS

| | | | |
|---|---|---|---|
| 4,210,391 | 7/1980 | Cohen | 351/161 |
| 4,338,005 | 7/1982 | Cohen | 351/161 |
| 4,340,283 | 7/1982 | Cohen | 351/161 |
| 4,637,697 | 1/1987 | Freeman | 351/161 |
| 4,641,934 | 2/1987 | Freeman | 351/159 |
| 4,642,112 | 2/1987 | Freeman | 623/6.3 |
| 4,655,565 | 4/1987 | Freeman | 351/159 |
| 4,981,342 | 1/1991 | Fiala | 359/494 |
| 5,024,517 | * 6/1991 | Seidner | 351/161 |
| 5,073,021 | * 12/1991 | Marron | 351/168 |
| 5,142,411 | 8/1992 | Fiala | 359/494 |
| 5,410,375 | 4/1995 | Fiala | 351/168 |
| 5,448,312 | 9/1995 | Roffman et al. | 351/161 |
| 5,485,228 | 1/1996 | Roffmna et al. | 351/161 |
| 5,682,223 | 10/1997 | Menezes et al. | 351/161 |
| 5,715,031 | 2/1998 | Roffman et al. | 351/161 |
| 5,805,260 | * 9/1998 | Roffman et al. | 351/161 |
| 5,835,192 | 11/1998 | Roffman et al. | 351/246 |
| 5,929,969 | 7/1999 | Roffman | 351/161 |
| 5,982,543 | * 11/1999 | Fiala | 351/159 |

FOREIGN PATENT DOCUMENTS

WO 99/34239    7/1999   (WO).

\* cited by examiner

Primary Examiner—Jordan M. Schwartz
(74) Attorney, Agent, or Firm—Lois Gianneschi

(57) ABSTRACT

The invention provides lenses incorporating both birefringent material and zones of more than one optical power, or focal length.

7 Claims, 1 Drawing Sheet

HYBRID REFRACTIVE BIREFRINGENT MULTIFOCAL OPHTHALMIC LENSES

FIELD OF THE INVENTION

The invention relates to multi-focal ophthalmic lenses. In particular, the invention provides lenses incorporating both birefringent material and zones of more than one optical power, or focal length.

BACKGROUND OF THE INVENTION

As an individual ages, the eye is less able to accommodate, or bend the natural lens, to focus on objects that are relatively near to the observer. This condition is known as presbyopia. Similarly, for persons who have had their natural lens removed and an intraocular lens inserted as a replacement, the ability to accommodate is totally absent.

Among the methods used to correct for the eye's failure to accommodate are lenses that have more than one optical power. In particular, contact and intraocular lenses have been developed in which zones of distance and near power are provided. These lenses are disadvantageous because they are difficult to manufacture. Additionally, the use of both distance and near power results in some loss of image contrast at each distance producing a less than completely clear image.

Another known method is to use diffractive simultaneous vision bifocal lenses which incorporate both diffractive optical elements and refractive elements. These lenses are disadvantageous in that light is lost to higher order diffraction. Additionally, the remaining light is split between distance and near vision resulting in less than clear images. Further, these lenses are extremely difficult to manufacture.

Yet another known method is to use birefringent material or a material with wo refractive indices. However, the known birefringent lenses are disadvantageous in use in that the image seen through the lens is not entirely clear.

Therefore, a need exists for a multifocal lens that overcomes some or all of the disadvantages of the prior art lenses.

DETAILED DESCRIPTION OF THE INVENTION AND PREFERRED EMBODIMENTS

The invention provides a multifocal lens, and methods for producing the lens, in which concentric, annular zones of differing power are used in combination with a birefringent material. The lenses of the invention provide a multifocal lens capable of providing clear vision at both near and far distances.

In one embodiment, the invention provides a lens comprising, consisting essentially of, and consisting of at least two concentric, annular zones of alternating refractive power and a birefringent material.

By "lens" is meant a contact, an intraocular lens, a corneal implant lens, an onlay lens, and the like, spectacle lens or combinations thereof. Preferably, the lenses of the invention are contact lenses.

Figure 2:
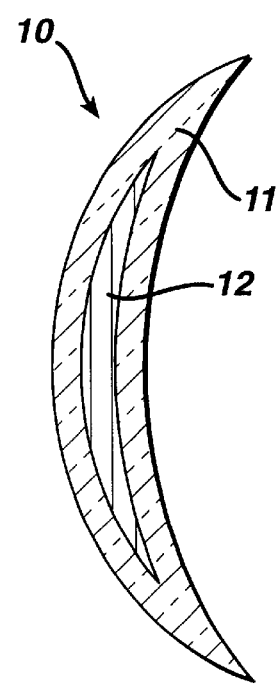
FIG. 2 depicts a magnified, cross-sectional view of the lens of claim through I—I

The birefringent material may form the lens itself Alternatively, the concave or convex surface of the lens may be formed from a birefringent material and the remainder of the lens formed from an isotropic material. As yet another alternative, and preferably, a birefringent material may be embedded within a non-birefringent lens material or an isotropic material. By "embedded" is meant that the birefringent material is substantially encased within the lens material. In FIG. 2 is depicted lens 10 composed of isotropic material 11 into which birefringent material 12 is embedded. Suitable birefringent materials for lens production are known and include, without limitation, organic polymers and polymers in which birefringence is induced by application of stress or stretching.

In embodiments in which an isotropic material is used in combination with a birefringent material, the isotropic materials may be any material useful for forming ophthalmic lenses. Preferably, the materials used are suitable for forming hard or, more preferably, soft contact lenses. Suitable soft contact lens materials include, without limitation, silicone elastomers, silicone-containing macromers including, without limitation, those disclosed in U.S. Pat. Nos. 5,371, 147, 5,314,960, and 5,057,578 incorporated herein in their entireties by reference, hydrogels, silicone-containing hydrogels, and the like and combinations thereof. More preferably, the surface of the contact lens is a siloxane, or contains a siloxane functionality, including, without limitation, polydimethyl siloxane macromers.

In the lenses in which the birefringent material is embedded within the lens, preferably, the birefringent material is embedded so that it is substantially wholly within the optic zone of the lens. Additionally, the birefringent material preferably is embedded within the bulk of the lens material to ensure wearer comfort. The embedded birefringent material may be introduced into the non-birefringent or isotropic lens material by any convenient method. For example, the birefringent material may be first formed and then surrounded by lens material by inserting it into a contact lens mold half into which lens material is then dispensed, introducing the other mold half, and curing the mold assembly. As another example, lens material may be dispensed into a mold half and partially cured followed by inserting the birefringent material onto the partially cured lens material, dispensing additional lens material, introducing the second mold half, and curing the mold assembly.

Figure 1:
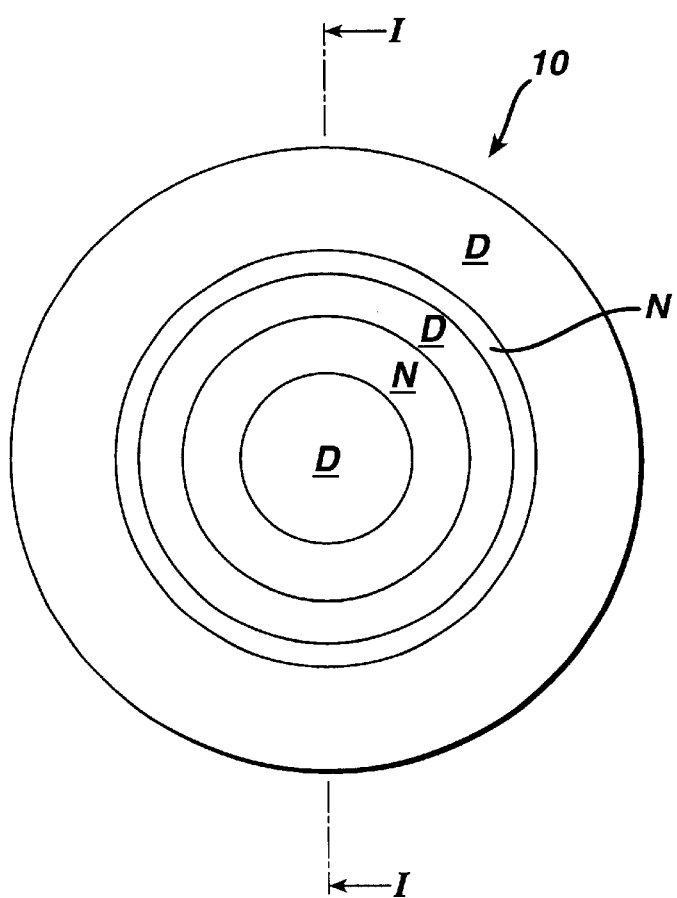
FIG. 1 depicts a magnified plan view of the concave surface of a lens of the invention.

In the lenses of the invention, at least two, concentric annular zones are provided. In the case of a contact lens, the annular zones will be within the lens' optic zone. One of the annular zones is of a refractive power substantially equal to the distance optical power, or power required to correct the lens wearer's distance vision acuity. The distance optical power zone alternates with a zone of refractive power substantially equal to that of the near optical power, or power required to correct the lens wearer's near vision acuity. In FIG. 1 is depicted the concave surface of lens 10 of the invention in which the alternating distance and near power annular zones are shown.

In one embodiment of the invention, a pair of lenses is provided in which the central portion of the optic zone of each lens provides optical power substantially equal to the distance optical power. Annular rings of alternating near and distance optical power surround this central optical zone. Alternatively, one lens may be as above-described, the other lens having a central zone with power substantially equal to the near optical power and surrounded with alternating near and distance optical power annular zones.

In a preferred embodiment, the invention provides a pair of ophthalmic lenses, one lens to be worn in the dominant eye and one to be worn in the non-dominant eye. By "dominant eye" is meant the eye that predominates for distance vision. The lens worn by the dominant eye has a surface, preferably the convex surface, with a central optic zone with substantially the desired distance optical power, and a surface, preferably the concave surface, that has at least two concentric annular zones in its optic zone. The power of each of the at least two annular zones is substantially equal to that of the distance optical power. Either or both the convex and concave surfaces may have additional annular zones with distance optical power, near optical power, or combinations thereof. Preferably, one surface, more preferably the convex surface, has only the central optical zone and no annular zones, the opposite surface, preferably the concave surface, in this embodiment having at least two annular zones of alternating distance and near optical power. Most preferably, the convex surface has only a central optical zone having the distance optical power, the concave surface having at least two zones of alternating distance and near optical powers.

Further in this embodiment, the lens worn by the non-dominant eye has a surface, preferably the convex surface, with a central optic zone with substantially the desired near optical power. The opposite surface, preferably the concave surface, has at least two concentric annular zones in its optic zone. The power of each of the at least two annular zones is substantially equal to that of the near optical power. Either or both the convex and concave surfaces have additional annular zones with distance optical power alternating with those having near optical power.

For the various contact lens embodiments, typically, the lens will be constructed with one or both non-optical lenticular and peripheral zones. The ratio of the contact lenses' optic zone to be devoted to distance and near optical power may be determined as disclosed in U.S. Pat. Nos. 5,929,969, 5,835,192, 5,715,031, 5,682,223, 5,485,228, and 5,448,312, incorporated herein in their entireties by reference.

In all embodiments of the lenses of the invention, the distance and near optical powers may be aspherical or spherical powers, but preferably are spherical. The lenses may have any of a number of a variety of corrective optical characteristics incorporated onto the surfaces in addition to distance and near optical powers, such as, for example, cylinder power.

The annular zone of the lenses of the invention may be formed by any conventional method. For example, contact lenses with the annular zones formed therein may be produced by diamond-turning using alternating radii. The zones may be diamond-turned into the molds that are used to form the lens of the invention. Subsequently, a suitable liquid resin is placed between the molds followed by compression and curing of the resin to form the lenses of the invention. Alternatively, the zones may be diamond-turned into lens buttons. Similarly, spectacle lenses may formed using molds with the zones formed therein. Additional methods for forming lenses are within the ordinary skill of the art of lens manufacture.

What is claimed is:

1. A first and a second contact lens for a lens wearer, the first lens comprising a birefringent material and a first convex and a first concave surface, the first convex surface comprising an optic zone comprising substantially all of the distance optical power and the first concave surface comprising an optic zone of at least two concentric, annular portions, the power of each of the at least two annular portions substantially equal to that of the distance optical power, and the second lens comprising a birefringent material and a second convex and a second concave surface, the second convex surface comprising an optic zone comprising substantially all of the near optical power and the second concave surface comprising an optic zone of at least two concentric, annular portions, the power of each of the at least two annular portions substantially equal to that of the near optical power.

2. A first and a second contact lens for a lens wearer, the first lens comprising a birefringent material and a first convex and a first concave surface, the first convex surface consisting essentially of an optic zone comprising substantially all of the distance optical power and the first concave surface comprising an optic zone of at least two concentric, annular portions of distance optical power, near optical power, or combinations thereof and the second lens comprising a birefringent material and a second convex and a second concave surface, the second convex surface consisting essentially of an optic zone comprising substantially all of the near optical power and the second concave surface comprising an optic zone of at least two concentric annular portions of distance optical power near optical power, or combinations thereof.

3. The first and second lenses of claim 1, wherein the optic zone of the concave surface of the first lens further comprises one or more annular portions of the near optical power and the optic zone of the concave surface of the second lens further comprises one or more annular portions of the distance optical power.

4. The first and second lenses of claim 1, wherein either or both the convex and concave surfaces of the first lens, second lens, or both lenses further comprise additional annular portions with distance optical power, near optical power, or combinations thereof.

5. The first and second lenses of claim 1, 2, 3, or 4 wherein the concave surface of the first lens, second lens, or both lenses comprising the birefringent material and the remainder of said first lens, said second lens, or both lenses comprise an isotropic material.

6. The first and second lenses of claim 1, 2, 3, or 4 wherein the convex surface of the first lens, second lens, or both lenses comprise the birefringent material and the remainder of said first lens, said second lens, or both lenses comprise an isotropic material.

7. The first and second lenses of claim 1, 2, 3, or 4 wherein the birefringent material is embedded within an isotropic lens material.

* * * * *